(12) United States Patent
Kammann et al.

(10) Patent No.: US 8,645,038 B2
(45) Date of Patent: Feb. 4, 2014

(54) METHOD AND DEVICE FOR DETERMINING A MAXIMUM COEFFICIENT OF FRICTION BETWEEN A TIRE AND AN UNDERLYING SURFACE

(75) Inventors: Stefan Kammann, Kelkheim (DE); Lothar Keller, Friedrichsdorf (DE)

(73) Assignee: Continental Automotive GmbH, Hannover (DE)

( * ) Notice: Subject to any disclaimer, the term of this patent is extended or adjusted under 35 U.S.C. 154(b) by 596 days.

(21) Appl. No.: 12/986,725

(22) Filed: Jan. 7, 2011

(65) Prior Publication Data

US 2011/0166761 A1 Jul. 7, 2011

(30) Foreign Application Priority Data

Jan. 7, 2010 (DE) .......................... 10 2010 004 113

(51) Int. Cl.
| | | |
|---|---|---|
| *G06F 7/70* | (2006.01) | |
| *G06F 19/00* | (2011.01) | |
| *G06G 7/00* | (2006.01) | |
| *G06G 7/76* | (2006.01) | |

(52) U.S. Cl.
USPC .............................................. 701/70; 702/41

(58) Field of Classification Search
USPC ........... 701/70, 72, 78, 80, 22, 82, 11, 83, 48; 702/41, 141, 10; 244/11; 180/19, 197, 180/408, 282; 303/15, 146
See application file for complete search history.

(56) References Cited

U.S. PATENT DOCUMENTS

| | | | | | |
|---|---|---|---|---|---|
| 4,180,223 | A | * | 12/1979 | Amberg ......................... | 244/111 |
| 5,163,530 | A | * | 11/1992 | Nakamura et al. ............ | 180/197 |
| 5,197,008 | A | * | 3/1993 | Itoh et al. ........................ | 701/70 |
| 5,255,192 | A | * | 10/1993 | Ito et al. .......................... | 701/90 |
| 5,307,274 | A | * | 4/1994 | Takata et al. .................... | 701/70 |
| 5,508,924 | A | * | 4/1996 | Yamashita ...................... | 701/22 |
| 5,513,907 | A | * | 5/1996 | Kiencke et al. ............... | 303/150 |
| 5,526,263 | A | * | 6/1996 | Tanaka et al. .................. | 701/70 |
| 5,576,959 | A | * | 11/1996 | Hrovat et al. ................... | 701/70 |
| 5,581,465 | A | * | 12/1996 | Adler et al. .................... | 701/110 |

(Continued)

FOREIGN PATENT DOCUMENTS

| | | |
|---|---|---|
| DE | 10338965 A1 | 3/2005 |
| DE | 102004053880 A1 | 5/2006 |
| DE | 102007062203 A1 | 6/2009 |
| WO | 2009080416 A1 | 7/2009 |

*Primary Examiner* — Thomas Black
*Assistant Examiner* — Robert Payne
(74) *Attorney, Agent, or Firm* — Laurence A. Greenberg; Werner H. Stemer; Ralph E. Locher

(57) ABSTRACT

A method for determining a maximum coefficient of friction $\mu_{max}$ between a tire and an underlying surface entails empirically determining a reference curve $\mu_{ref}(S)$ of a coefficient of friction $\mu_{ref}$ as a function of a slip S between the tire and an underlying reference surface, determining a first momentary slip $S_1$ for the tire and a first momentary coefficient of friction $\mu_1$ between the tire and the underlying surface at a first instant $t_1$, determining a second momentary slip $S_2$ for the tire and a second momentary coefficient of friction $\mu_2$ between the tire and the underlying surface at a second instant $t_2$, computing a slope of the curve $\mu(S)$ of the coefficient of friction $\mu$ as a function of slip S, and computing the maximum coefficient of friction $\mu_{max}$ between the tire and the underlying surface by transforming the reference curve $\mu_{ref}(S)$ on the basis of the slope of the curve $\mu(S)$.

17 Claims, 2 Drawing Sheets

(56) References Cited

U.S. PATENT DOCUMENTS

| | | | |
|---|---|---|---|
| 5,701,248 A * | 12/1997 | Wanke | 701/70 |
| 5,710,704 A * | 1/1998 | Graber | 701/82 |
| 5,711,023 A * | 1/1998 | Eckert et al. | 701/70 |
| 5,711,024 A * | 1/1998 | Wanke | 701/82 |
| 5,742,507 A * | 4/1998 | Eckert | 701/70 |
| 5,826,210 A * | 10/1998 | Izumi et al. | 701/70 |
| 5,869,742 A * | 2/1999 | Koster et al. | 73/9 |
| 6,061,642 A * | 5/2000 | Nakajima | 702/105 |
| 6,092,014 A | 7/2000 | Okada | 701/70 |
| 6,208,927 B1 * | 3/2001 | Mine et al. | 701/70 |
| 6,216,079 B1 * | 4/2001 | Matsuda | 701/70 |
| 6,278,929 B1 * | 8/2001 | Tozu et al. | 701/70 |
| 6,401,023 B1 * | 6/2002 | Takahashi | 701/70 |
| 6,415,215 B1 * | 7/2002 | Nishizaki et al. | 701/70 |
| 6,456,920 B1 * | 9/2002 | Nishio et al. | 701/70 |
| 6,463,378 B2 * | 10/2002 | Nishio | 701/70 |
| 6,618,663 B2 * | 9/2003 | Aga | 701/83 |
| 6,671,604 B1 * | 12/2003 | Frentz et al. | 701/70 |
| 6,810,317 B2 * | 10/2004 | Sauter et al. | 701/70 |
| 6,839,615 B2 * | 1/2005 | Yanase | 701/1 |
| 6,868,324 B2 * | 3/2005 | Matsumoto et al. | 701/72 |
| 6,892,123 B2 * | 5/2005 | Hac | 701/48 |
| 6,904,349 B2 * | 6/2005 | Mori | 701/70 |
| 6,904,351 B1 * | 6/2005 | Hac | 701/70 |
| 6,922,624 B2 * | 7/2005 | Isaji et al. | 701/70 |
| 6,971,726 B2 * | 12/2005 | Levy et al. | 303/150 |
| 7,139,650 B2 * | 11/2006 | Lubischer | 701/48 |
| 7,191,047 B2 * | 3/2007 | Chen et al. | 701/70 |
| 7,206,702 B2 * | 4/2007 | Isono et al. | 702/41 |
| 7,248,958 B2 * | 7/2007 | Watanabe et al. | 701/70 |
| 7,315,777 B2 * | 1/2008 | Ono | 701/70 |
| 7,451,032 B2 * | 11/2008 | Brown et al. | 701/70 |
| 7,509,204 B2 * | 3/2009 | Phillips et al. | 701/70 |
| 7,620,504 B2 * | 11/2009 | Ogawa | 702/41 |
| 7,680,577 B2 * | 3/2010 | Mori | 701/70 |
| 7,734,406 B1 * | 6/2010 | Oppenheimer et al. | 701/70 |
| 8,027,775 B2 * | 9/2011 | Takenaka et al. | 701/70 |
| 8,086,382 B2 * | 12/2011 | Dagenais et al. | 701/70 |
| 8,155,852 B2 * | 4/2012 | Takenaka et al. | 701/70 |
| 8,271,175 B2 * | 9/2012 | Takenaka et al. | 701/71 |
| 2001/0053953 A1 * | 12/2001 | Gong et al. | 701/70 |
| 2003/0195690 A1 * | 10/2003 | Batistic et al. | 701/72 |
| 2004/0186648 A1 * | 9/2004 | Zheng et al. | 701/70 |
| 2005/0038588 A1 * | 2/2005 | Shukla | 701/70 |
| 2011/0106458 A1 * | 5/2011 | Shiozawa et al. | 702/41 |
| 2011/0166761 A1 * | 7/2011 | Kammann et al. | 701/70 |

* cited by examiner

METHOD AND DEVICE FOR DETERMINING A MAXIMUM COEFFICIENT OF FRICTION BETWEEN A TIRE AND AN UNDERLYING SURFACE

CROSS-REFERENCE TO RELATED APPLICATION

This application claims the priority, under 35 U.S.C. §119, of German patent application DE 10 2010 004 113.0, filed Jan. 7, 2010; the prior application is herewith incorporated by reference in its entirety.

BACKGROUND OF THE INVENTION

Field of the Invention

The invention relates to a method and a device for determining a maximum coefficient of friction $\mu_{max}$ between a tire and an underlying surface. Knowing the maximum coefficient of friction means that an increased risk of an additional potential longitudinal or transverse slip of the tire may be taken into account in motor-vehicle electronics.

How to specify a maximum coefficient of friction as an estimated value on the basis of customary asphalt pavements and typical tires is already known. What is disadvantageous therein is that a maximum coefficient of friction specified through estimating is extremely imprecise and only seldom reflects the actual conditions with sufficient accuracy.

SUMMARY OF THE INVENTION

It is accordingly an object of the invention to provide a method and a device for determining a maximum coefficient of friction $\mu_{max}$ between a tire and an underlying surface which overcome the above-mentioned disadvantages of the heretofore-known devices and methods of this general type and which allows for the maximum coefficient of friction $\mu_{max}$ to be determined more accurately.

With the foregoing and other objects in view there is provided, in accordance with the invention, a method of determining a maximum coefficient of friction $\mu_{max}$ between a tire and an underlying surface, the method which comprises:

empirically determining a reference curve $\mu_{ref}(S)$ of a coefficient of friction $\mu_{ref}$ as a function of a slip S between the tire and an underlying reference surface;

determining a first momentary slip $S_1$ for the tire and a first momentary coefficient of friction $\mu_1$ between the tire and the underlying surface at a first instant $t_1$;

determining a second momentary slip $S_2$ for the tire and a second momentary coefficient of friction $\mu_2$ between the tire and the underlying surface at a second instant $t_2$;

computing a slope of the momentary curve $\mu(S)$ of the coefficient of friction $\mu$ as a function of the slip S; and computing the maximum coefficient of friction $\mu_{max}$ between the tire and the underlying surface by transforming the reference curve $\mu_{ref}(S)$ on the basis of the slope of the curve $\mu(S)$.

In other words, the objects of the invention are achieved with a novel method for determining a maximum coefficient of friction $\mu_{max}$ between a tire and an underlying surface that entails empirically determining a reference curve $\mu_{ref}(S)$ of a coefficient of friction $\mu_{ref}$ as a function of a slip S between the tire and an underlying surface, determining a first momentary slip $S_1$ for the tire and a first momentary coefficient of friction $\mu_1$ between the tire and the underlying surface at a first instant $t_1$, determining a second momentary slip $S_2$ for the tire and a second momentary coefficient of friction $\mu_2$ between the tire and the underlying surface at a second instant $t_2$, computing a slope in the momentary curve $\mu(S)$ of the coefficient of friction $\mu$ as a function of the slip S, and computing the maximum coefficient of friction $\mu_{max}$ between the tire and the underlying surface by transforming the reference curve $\mu_{ref}(S)$ on the basis of the slope in the curve $\mu(S)$.

With the aid of the vehicle devices that are present in any event in modern motor vehicles it is possible to use the information provided by the vehicle devices such as, for example, by vehicle control devices such as ABS, ESP, ESC, and/or a tire control system to be able to compute the momentary slip S and the momentary coefficient of friction $\mu$. By comparing the momentary curve $\mu(S)$ that can be determined from the measuring points ($\mu_1$; $S_1$) and ($\mu_2$; $S_2$) with the empirically determined reference curve $\mu_{ref}(S)$ it is possible using a suitable mathematical method to very accurately estimate, in particular interpolate, the maximum coefficient of friction $\mu_{max}$ for the momentary material pairing of the tire with the underlying surface. That enables prompt account to be taken of changing frictional characteristics of the underlying surface particularly when the underlying surface is changing. A clearly too-risky assumption for the maximum coefficient of friction $\mu_{max}$ or a clearly too conservative assumption for the maximum coefficient of friction $\mu_{max}$ will be avoided thereby. It will simultaneously be possible to take account automatically of frictional characteristics of the tire that change owing to, for example, different air pressures, different tire temperatures, and/or wear and tear. A motor vehicle's driving systems will be enabled thereby to allow for a non-ideal tire pressure and/or signs of ageing and/or signs of wear and tear in the tire when monitoring traveling situations of the motor vehicle. Prompt intervention by a drive-control system such as in the case of, for example, ABS, ESP, or ESC can be insured thereby and unnecessary intervention by a drive system avoided. Driving safety will be enhanced thereby with no adverse effect on driving convenience.

For determining the reference curve a multiplicity of tests can be conducted for a specific type of tire, particularly on an identical underlying surface, to obtain a multiplicity of measuring points that include both the region of static friction and the transition to sliding friction. The slip S can be determined for the respective tire with the aid of, for instance, a wheel-speed sensor by computing the rotational speed of the respective wheel $\omega$ and the rotational speed of a wheel $\omega_0$ that is entrained in an idling fashion, using the formula:

$$S = \frac{\omega - \omega_0}{\omega_0}$$

The momentarily acting coefficient of friction $\mu$ is computed from the ratio between the normal force $F_N$ acting in the respective tire and the transverse force $F_X$ acting transversally thereto. The normal force $F_N$ for the respective tire is a portion z of the absolute load at rest being the product of the vehicle's mass m and the force of Earth's gravity g. For the transverse force $F_X$, what operates from the overall acceleration force as computed from the vehicle's mass m and its acceleration a is a relative acceleration component w so that $$\mu = \frac{F_N}{F_X} = \frac{z \cdot m \cdot g}{w \cdot m \cdot a} = \frac{z \cdot g}{w \cdot a}$$

is produced as the coefficient of friction. The respective parameters for computing the coefficient of friction $\mu$ are either already known or can be determined from the customarily present driving systems and made available. For determining the momentary slip and the momentary coefficient of friction $\mu$, the measuring instants $t_1$ and $t_2$ are sufficiently far apart in time to be able to determine the slope of the curve of a changing slip with sufficient accuracy. The measuring instants $t_1$ and $t_2$ are in particular sufficiently close together in time to have been assigned with high probability to the same acceleration process and/or the same braking process. It is furthermore possible to determine the momentary slip S and momentary coefficient of friction $\mu$ substantially continuously and use measured values that are sufficiently far apart for customary measurement inaccuracies not to be able to significantly adversely affect the slope's correct computation. One of the measuring instants $t_1$ or $t_2$ is particularly preferably an instant at which the tire is not revolving and the coefficient of friction $\mu$ and the slip S will by definition be zero. This zero point can also be specified as one of the measuring instants so that it is possible to compare the momentary measurement with the zero point in order to determine the slope of p(S). In the event that the momentary conditions are sufficiently close to the computed maximum coefficient of friction $\mu_{max}$, the zero point will additionally or alternatively no longer be taken into account but, instead, preferably a multiplicity of momentary measuring points so that account can be taken of a non-linear curve p(S) in the measured range.

What is particularly preferably determined is a maximum coefficient of friction $\mu_{max,x}$ in the direction of the tire's travel and a maximum coefficient of friction $\mu_{max,y}$ transverse to the tire's direction of travel. Account can thereby be taken of the fact that tires usually have different adhesion characteristics in the direction of travel and transversely thereto. It will in particular be possible to separately assess the risk of a tire's skidding or spinning while moving in a straight line on the one hand and round a bend on the other. Account can likewise be taken thereby of a motor vehicle's possible swerving or floating.

Affine mapping of the reference curve $\mu_{ref}(S)$ preferably takes place while said curve is being transformed, with in particular exclusively mathematical rotating and mathematical scaling of the reference curve $\mu_{ref}(S)$ taking place. That makes it possible to map the reference curve $\mu_{ref}(S)$ onto the momentary actual curve using simple mathematical computations and to read the mapped maximum coefficient of friction $\mu_{max}$. The parameters for performing said affine mapping can in particular be determined on the basis of the determined slope of the actual curve of $\mu(S)$. In particular, if only the momentary maximum coefficient of friction $\mu_{max}$ is to be computed, it will suffice to transform just the point for the maximum coefficient of friction $\mu_{max}$ of the reference curve $\mu_{ref}(S)$ to directly obtain the momentary actual maximum coefficient of friction $\mu_{max}$.

Preferably a plurality of reference curves $\mu_{ref}(S)$ will be empirically determined as a function of tire wear and tear. The momentary tire wear and tear will be determined with the aid of a tire control system, which in particular determines a tire-profile depth of the tire, and the reference curve $\mu_{ref}(S)$ corrected on the basis of the momentary tire wear and tear with the aid of the further reference curves $\mu_{ref}(S)$. That will enable the tire wear and tear already to be taken into account in the reference curve $\mu_{ref}(S)$. The maximum coefficient of friction $\mu_{max}$ can consequently be determined with greater accuracy. More complex computations of the tire wear and tear in determining the momentary maximum coefficient of friction $\mu_{max}$ will as a result be unnecessary. Computing the maximum coefficient of friction $\mu_{max}$ will be simplified thereby and can be performed faster.

Preferably tire data, in particular tire dimensions, tire type, tire pressure, tire temperature, and/or tire-profile depth will be determined with the aid of a tire control system and the reference curve $\mu_{ref}(S)$ corrected with the aid of the tire data to take account of tire data deviating from the momentary tire data when determining the reference curve $\mu_{ref}(S)$. It is thereby possible to allow for the fact that the tire data used for empirically determining the reference curve $\mu_{ref}(S)$ may differ from that used for the momentary measurement. For example the momentary tire pressure can be lower than the tire pressure applying when the reference curve $\mu_{ref}(S)$ is determined empirically. Using suitable correction factors will enable thus differing conditions that influence the frictional characteristics of the tire/underlying surface material pairing to be taken into account. Suitable correction factors can be determined experimentally as a function of the parameter requiring to be taken into account.

In particular a relative acceleration component is determined with the aid of a vehicle control device during a braking and/or an accelerating action. With the aid of a vehicle control device suitable therefor it can be determined which tire absorbs the occurring acceleration forces to what extent during an accelerating or braking action. Data of such kind can be provided by, for example, a vehicle control device whose function is to prevent the motor vehicle from skidding such as ESP, for instance.

Preferably a more relative wheel load is determined with the aid of a tire control system that in particular provides tire stand surface data (i.e., the surface of the tire that is momentarily supported on and touching the underlying surface) and/or pressure data and/or tire data. In particular an uneven distribution of the motor vehicle's weight over a plurality of tires can be taken into account thereby. For determining the relative wheel load for example the extent of deformation during a wheel rotation of the tire compared with other tires can be determined.

In particular the tire's slip is determined with the aid of a wheel-speed sensor. With the aid of the wheel-speed sensor it is possible to determine the tire's momentary rotational speed and the rotational speed of a tire that is entrained in an idling fashion.

The determined maximum coefficient of friction $\mu_{max}$ is made available particularly preferably to a drive-regulating system, especially ABS, ESP, ESC, and/or—via a CAN bus—to motor-vehicle systems. This enables driving systems which for their operation require at least one estimated value for the maximum coefficient of friction to be supplied with very precise information about the momentary maximum coefficient of friction $\mu_{max}$. Due to the fact that the maximum coefficient of friction $\mu_{max}$ is determined anew in an ongoing fashion, the driving systems are enabled to take account of changing frictional conditions without needing an additional separate sensor system therefor. The driving systems' operating mode is improved thereby. Desired safety reserves can furthermore be more precisely determined and maintained.

With the above and other objects in view there is also provided, in accordance with the invention, a device for determining a maximum coefficient of friction $\mu_{max}$ between a tire and an underlying surface, in particular a device for carrying out the above-outlined method. The device comprises:

a non-volatile memory with an empirically determined reference curve $\mu_{ref}(S)$ of a coefficient of friction $\mu_{ref}$ as a function of a slip S between the tire and an underlying reference surface;

a measuring system for determining a first momentary slip $S_1$ for the tire and a first momentary coefficient of friction $\mu_1$ between the tire and the underlying surface at a first instant $t_1$ and for determining a second momentary slip $S_2$ for the tire and a second momentary coefficient of friction $\mu_2$ between the tire and the underlying surface at a second instant $t_2$; and a computing unit for computing a slope of the curve $\mu(S)$ of the coefficient of friction $\mu$ as a function of a slip S and for computing the maximum coefficient of friction $\mu_{max}$ between the tire and the underlying surface by transforming the reference curve $\mu_{ref}(S)$ on the basis of the slope of the curve $\mu(S)$.

In other words, the novel device has a non-volatile memory having a stored empirically determined reference curve $\mu_{ref}(S)$ of a coefficient of friction $\mu_{ref}$ as a function of a slip S between the tire and an underlying reference surface. Further provided is a measuring system for determining a first momentary slip $S_1$ for the tire and a first momentary coefficient of friction $\mu_1$ between the tire and the underlying surface at a first instant $t_1$ and for determining a second momentary slip $S_2$ for the tire and a second momentary coefficient of friction $\mu_2$ between the tire and the underlying surface at a second instant $t_2$. The device further has a computing unit for computing a slope in the momentary curve $\mu(S)$ of the coefficient of friction $\mu$ as a function of the slip S and for computing the optimum coefficient of friction $\mu_{max}$ between the tire and the underlying surface by transforming the reference curve $\mu_{ref}(S)$ on the basis of the slope of the curve $\mu(S)$. The device can in particular be embodied and developed as described above with reference to the inventive method. With the aid of the vehicle devices present in any event in modern motor vehicles it is possible to use the information provided by the vehicle devices such as, for example, by vehicle control devices such as ABS, ESP, ESC, and/or a tire control system to be able to compute the momentary slip S and the momentary coefficient of friction $\mu$. By comparing the momentary curve $\mu(S)$ that can be determined from the measuring points ($\mu_1$; $S_1$) and ($\mu_2$; $S_2$) with the empirically determined reference curve $\mu_{ref}(S)$ it is possible using a suitable mathematical method to very accurately estimate, in particular interpolate, the maximum coefficient of friction $\mu_{max}$ for the momentary material pairing of the tire with the underlying surface.

Other features which are considered as characteristic for the invention are set forth in the appended claims.

Although the invention is illustrated and described herein as embodied in a method and device for determining a maximum coefficient of friction $\mu_{max}$ between a tire and an underlying surface, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
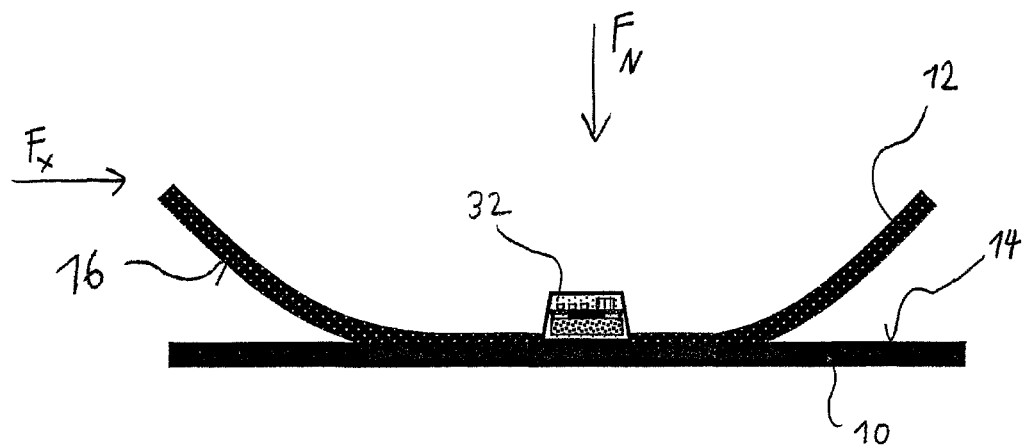
FIG. 1 is a schematic side view of a tire on an underlying surface having a device for determining a maximum coefficient of friction.

Referring now to the figures of the drawing in detail and first, particularly, to FIG. 1 thereof, a normal force $F_N$ is applied in the vertical direction to a tire 12 rolling along an underlying surface 10. The force $F_N$ is substantially a portion z of the weight force of a motor vehicle having the mass m at a force of Earth's gravity g. A transverse force $F_X$ operates on the tire 12 in the horizontal direction, with a relative acceleration component w of the acceleration force of the motor vehicle having the mass m and the acceleration a operating on the tire 12. The coefficient of friction $\mu$ developing between a top 14 of the underlying surface 10 and an outer surface 16 of the tire 12 is obtained according to the formula:

$$\mu = \frac{F_N}{F_X} = \frac{z \cdot m \cdot g}{w \cdot m \cdot a} = \frac{z \cdot g}{w \cdot a}.$$

A slip S resulting between the top 14 of the underlying surface 10 and the outer side 16 of the tire 12 between the tire 12 and the underlying surface 14 is determined by the rotational speed of tire $\omega$ and the rotational speed of a tire $\omega_0$ entrained in an idling fashion according to the formula:

$$S = \frac{\omega - \omega_0}{\omega_0}$$

Figure 2:
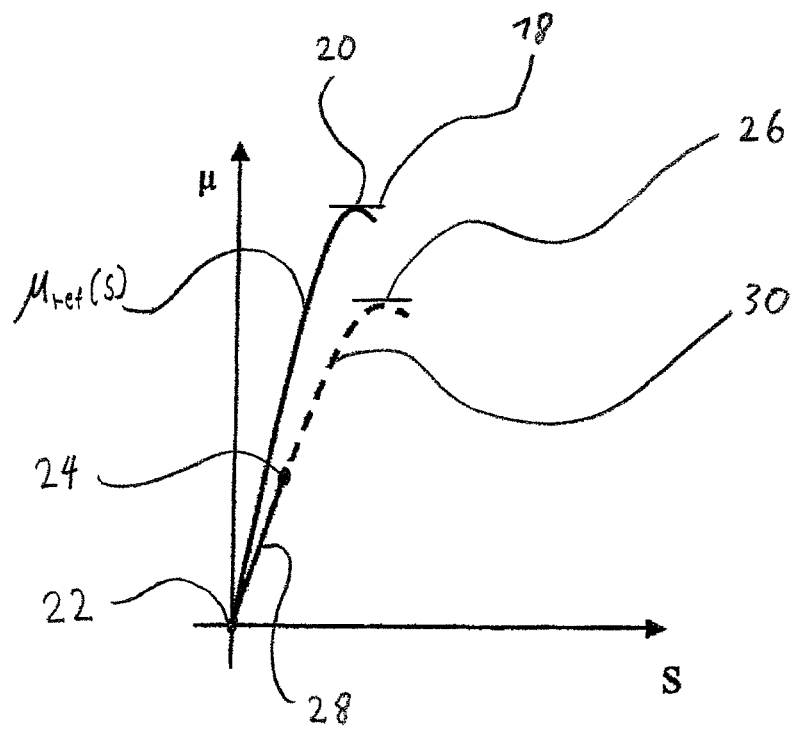
FIG. 2 is a schematic plot of a curve of a coefficient of friction $\mu$ as a function of a slip S in a first traveling situation.

FIG. 2 shows an empirically determined reference curve $\mu_{ref}(S)$ of a coefficient of friction $\mu$ as a function of a slip S. The maximum coefficient of friction $\mu_{max}$ of the reference curve $\mu_{ref}(S)$ is at a point 20 of the reference curve $\mu_{ref}(S)$ identified by a horizontal tangent 18. First point 20 therein identifies the transition from static friction (left-hand side) to sliding friction (right-hand side) between the tire 12 and the underlying surface 10. A different curve of the coefficient of friction $\mu$ occurs as a function of the slip S at frictional conditions deviating from the reference curve $\mu_{ref}(S)$. For computing the actual curve $\mu(S)$ the momentary coefficient of friction $\mu$ and the momentary slip S are determined at a first measuring point 22 with a second measuring point 24. At a first instant $t_1$, measured values ($\mu_1$; $S_1$) that determine first measuring point 22 are determined for the coefficient of friction $\mu$ and the slip S. Analogously, at a second instant $t_2$, measured values ($\mu_2$; $S_2$) that determine second measuring point 24 are determined for the coefficient of friction $\mu$ and the slip S. In the exemplary embodiment shown, the first measuring point 22 coincides with the zero point so that no measuring is required for the first measuring point 22 because the values for the coefficient of friction $\mu$ and the slip S are by definition zero at the zero point. For determining the actual maximum coefficient of friction 26 a slope 28 is determined between the measuring points 22, 24 and the further curve of $\mu(S)$ computed by comparing a slope 28 with the reference curve $\mu_{ref}(S)$ so that a computed curve 30 is produced from which the actual maximum coefficient of friction 26 can be read. For the traveling situation shown in FIG. 2 a lower momentary maximum coefficient of friction 26 results from comparing the momentary curve $\mu(S)$ with the reference curve $\mu_{ref}(S)$. That could be the case if, for instance, the reference curve $\mu_{ref}(S)$ was determined during dry weather and in the case of the traveling situation shown in FIG. 2 an underlying surface 10 is wet from rain.

Figure 3:
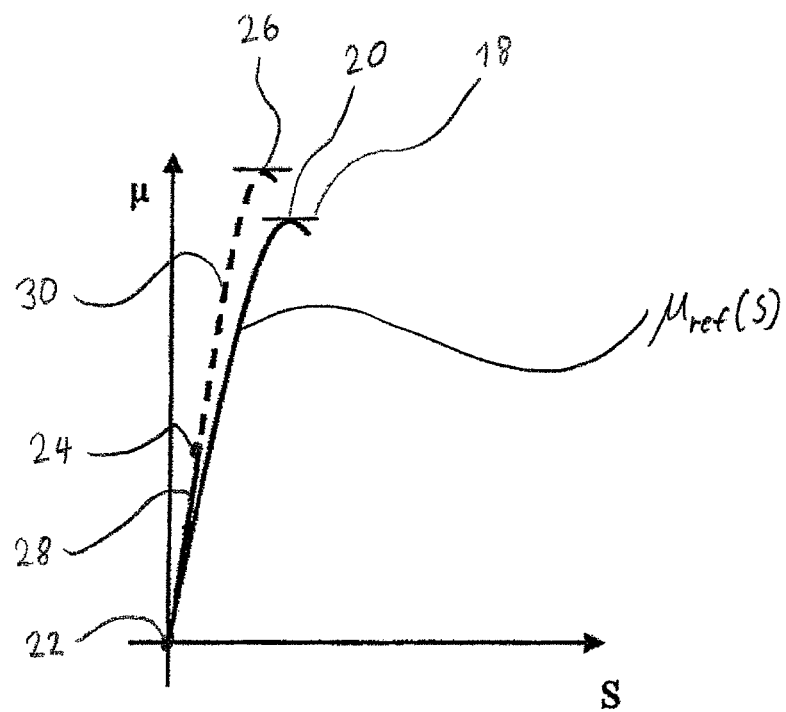
FIG. 3 is a schematic plot of a curve of a coefficient of friction $\mu$ as a function of a slip S in a second traveling situation.

For the traveling situation shown in FIG. 3 a higher maximum coefficient of friction 26 results from the momentary curve μ(S) compared with the reference curve $\mu_{ref}(S)$. That could be the case, for example, if an underlying surface 10 is sticky or adheres better than when the reference curve $\mu_{ref}(S)$ was empirically determined.

Figure 4:
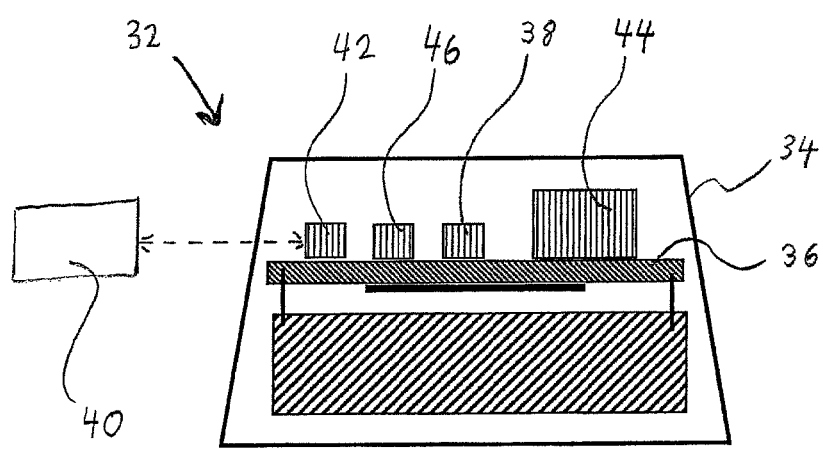
FIG. 4 is a schematic sectional view of the device for determining a maximum coefficient of friction shown in FIG. 1.

The maximum coefficient of friction 26 can be computed by means of a device 32 shown in FIG. 4 that can be located inside or outside tire 12. The device 32 can be a part of a tire sensor that is provided in any event in tire 12. The device 32 illustrated here has a housing 34 in which a non-volatile memory 38 is connected to a printed-circuit board 36. The reference curve $\mu_{ref}(S)$ individually determined for tire 12 is safely stored in the non-volatile memory 38. The slip S can be determined from the momentary angular velocity of the tire 12 with the aid of a measuring system 40 and transmitted to a transmitter/receiver unit 42, in particular wirelessly, for example by radio. The transmitter/receiver unit 42 is connected to a computing unit 44 via printed-circuit board 36, with its being possible for the data that is obtained to be temporarily stored particularly in a buffer 46. The computing unit 44 can compute, by way of a comparison with the stored reference curve $\mu_{ref}(S)$, the maximum coefficient of friction $\mu_{max}$ between the tire 12 and the underlying surface 10 from data that is obtained about the slip S. The device 32 is powered with the aid of a battery 48 that is electrically connected to the printed-circuit board 36.

The invention claimed is:

1. A method of determining a maximum coefficient of friction $\mu_{max}$ between a tire and an underlying surface, the method which comprises:
    empirically determining a reference curve $\mu_{ref}(S)$ of a coefficient of friction $\mu_{ref}$ as a function of a slip S between the tire and an underlying reference surface;
    determining a first momentary slip $S_1$ for the tire and a first momentary coefficient of friction $\mu_1$ between the tire and the underlying surface at a first instant $t_1$;
    determining a second momentary slip $S_2$ for the tire and a second momentary coefficient of friction $\mu_2$ between the tire and the underlying surface at a second instant $t_2$;
    computing a slope of the momentary curve μ(S) of the coefficient of friction μ as a function of the slip S; and
    computing the maximum coefficient of friction $\mu_{max}$ between the tire and the underlying surface by transforming the reference curve $\mu_{ref}(S)$ on the basis of the slope of the curve μ(S).

2. The method according to claim 1, which further comprises integrating the maximum coefficient of friction $\mu_{max}$ between the tire and the underlying surface in a drive-control system influencing a drive behavior of a motor vehicle.

3. The method according to claim 1, which comprises determining a maximum coefficient of friction $\mu_{max,x}$ in a direction of travel of the tire and a maximum coefficient of friction $\mu_{max,y}$ transverse to a direction of travel of the tire.

4. The method according to claim 1, wherein the transforming step comprises carrying out affine mapping of the reference curve $\mu_{ref}(S)$.

5. The method according to claim 4, which comprises subjecting the reference curve $\mu_{ref}(S)$ to exclusively mathematical rotatation and mathematical scaling.

6. The method according to claim 1, which comprises empirically determining a plurality of further reference curves $\mu_{ref}(S)$ as a function of tire wear and tear, determining a momentary tire wear and tear with the aid of a tire control system, and correcting the reference curve $\mu_{ref}(S)$ on a basis of the momentary tire wear and tear with the aid of the further reference curves $\mu_{ref}(S)$.

7. The method according to claim 6, wherein the tire control system determines a tire-profile depth of the tire.

8. The method according to claim 1, which comprises determining tire data selected from the group consisting of tire dimensions, tire type, tire pressure, tire temperature, and tire-profile depth with a tire control system and correcting the reference curve $\mu_{ref}(S)$ based on the tire data to take account of tire data deviating from momentary tire data when determining the reference curve $\mu_{ref}(S)$.

9. The method according to claim 1, which comprises determining a relative acceleration component with a vehicle control device during a braking and/or an accelerating action.

10. The method according to claim 1, which comprises determining a relative wheel load.

11. The method according to claim 10, which comprises determining with the tire control system one or more of data concerning a surface of the tire momentarily supported on the underlying surface, pressure data, or tire data.

12. The method according to claim 1, which comprises determining a slip S of the tire by way of a wheel-speed sensor.

13. The method according to claim 1, which comprises making the maximum coefficient of friction $\mu_{max}$ thus determined available to a drive-regulating system of a motor vehicle.

14. The method according to claim 13, which comprises further utilizing the maximum coefficient of friction $\mu_{max}$ thus determined in a vehicle system selected from the group consisting of ABS, ESP, ESC.

15. The method according to claim 13, which comprises transmitting the maximum coefficient of friction $\mu_{max}$ thus determined via a CAN bus within the motor vehicle.

16. A device for determining a maximum coefficient of friction $\mu_{max}$ between a tire and an underlying surface, comprising:
    a non-volatile memory having stored therein an empirically determined reference curve $\mu_{ref}(S)$ of a coefficient of friction $\mu_{ref}$ as a function of a slip S between the tire and an underlying reference surface;
    a measuring system for determining a first momentary slip $S_1$ for the tire and a first momentary coefficient of friction $\mu_1$ between the tire and the underlying surface at a first instant $t_1$ and for determining a second momentary slip $S_2$ for the tire and a second momentary coefficient of friction $\mu_2$ between the tire and the underlying surface at a second instant $t_2$; and
    a computing unit for computing a slope of the curve μ(S) of the coefficient of friction μ as a function of a slip S and for computing the maximum coefficient of friction $\mu_{max}$ between the tire and the underlying surface by transforming the reference curve $\mu_{ref}(S)$ on the basis of the slope of the curve μ(S).

17. The device according to claim 16, configured for carrying out the method according to claim 1.

* * * * *